United States Patent [19]

Van De Weghe

[11] Patent Number: 4,606,736

[45] Date of Patent: Aug. 19, 1986

[54] COVER ASSEMBLY FOR CLOSED BODILY FLUID DRAINAGE UNIT

[75] Inventor: Mary R. Van De Weghe, Ridgewood, N.J.

[73] Assignee: Van De Weghe Associates, Inc., Ridgewood, N.J.

[21] Appl. No.: 693,795

[22] Filed: Jan. 23, 1985

[51] Int. Cl.⁴ ............................................. A61M 1/00
[52] U.S. Cl. ................................... 604/322; 604/327; D24/58
[58] Field of Search ............... 604/262, 403, 408, 410, 604/322, 327–337; D24/51, 52, 54, 56, 58; 128/DIG. 15

[56] References Cited

U.S. PATENT DOCUMENTS

| | | | |
|---|---|---|---|
| D. 228,965 | 10/1973 | Dube | D24/54 |
| D. 245,119 | 7/1977 | Harris | D24/58 |
| D. 270,091 | 8/1983 | Setzer | D24/58 |
| 1,730,983 | 10/1929 | Sandig | 604/262 |
| 3,897,785 | 8/1975 | Barto, Jr. | 604/327 |
| 4,173,979 | 11/1979 | Odis | 604/327 |
| 4,439,191 | 3/1984 | Hogan | 604/332 |
| 4,495,662 | 1/1985 | Miller | 604/332 |
| 4,511,358 | 4/1985 | Johnson, Jr. et al. | 604/327 |
| 4,519,797 | 5/1985 | Hall | 604/337 |

*Primary Examiner*—C. Fred Rosenbaum
*Assistant Examiner*—Michelle Lester
*Attorney, Agent, or Firm*—Stefan J. Klauber

[57] ABSTRACT

An enclosure is disclosed for use with a bodily fluid drainage unit of the type comprising a flexible plastic bag having an upwardly extending flexible filler tube connectible to a patient for receiving bodily fluids, and hanger means extending from the upper end of same for enabling attachment to a receiving surface associated with the patient's environment. The enclosure receives the drainage unit therein to attractively conceal same, while simultaneously not impairing the functioning of the said unit. The enclosure is a generally flattened flexible envelope openable along one end for receiving the drainage unit. The openable end is provided on its opposed facing edges with mateable closures which enable closure of that end, and enable simultaneous nesting of the upwardly extending flexible filler tube of said drainage unit by the surrounding closure means. The envelope is provided at one flattened surface, and adjacent to the openable end, with one or more buttonhole type openings extending through the envelope into the interior of same. These openings are alignable with the hanger means of the drainage unit emplaced within the envelope, to receive the hanger means through the openings, to enable the hanging functioning of same.

10 Claims, 10 Drawing Figures

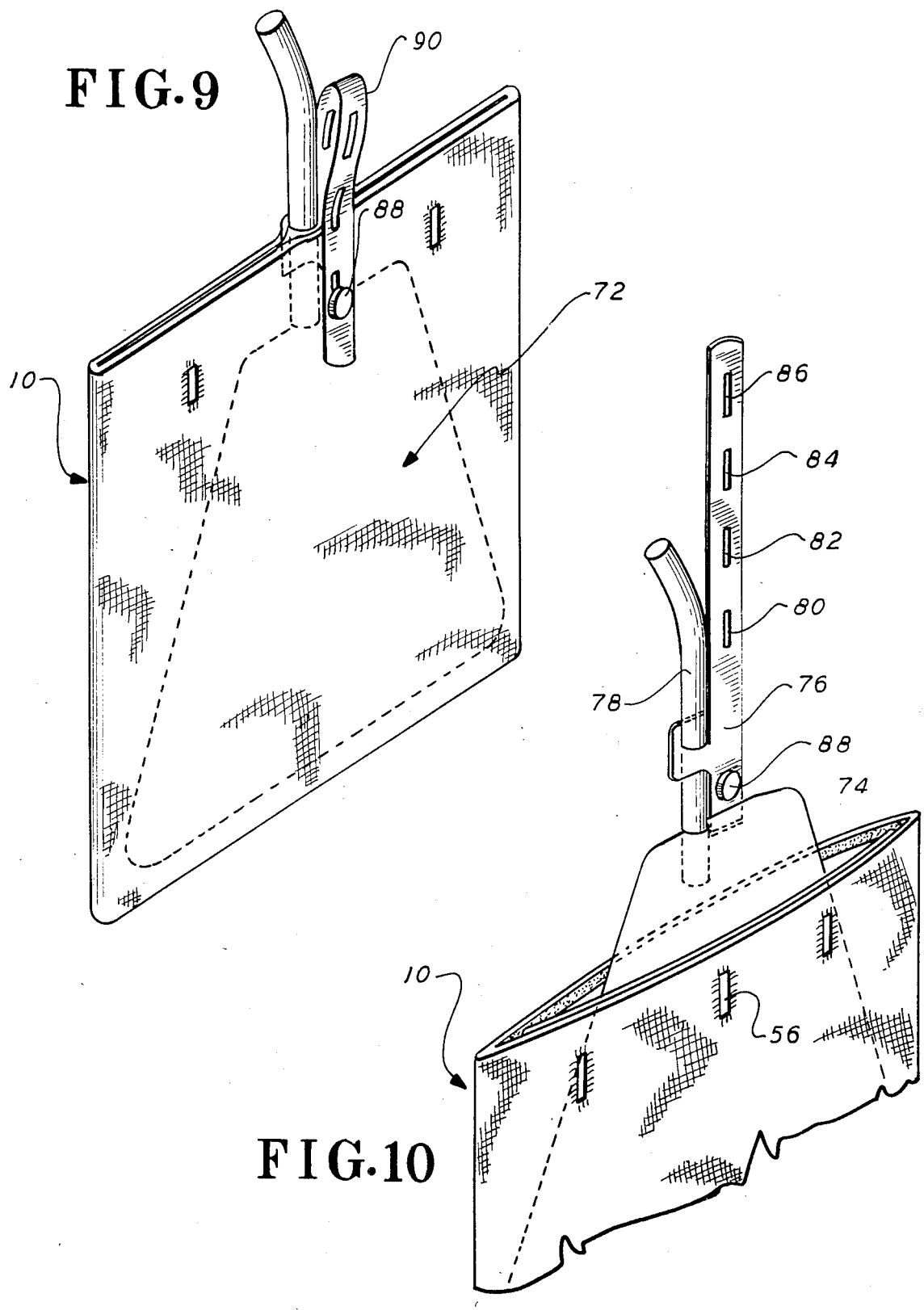

COVER ASSEMBLY FOR CLOSED BODILY FLUID DRAINAGE UNIT

BACKGROUND OF INVENTION

The present invention relates generally to devices for use with bodily fluid drainage units, and more specifically, relates to a protective and attractive cover intended for receipt of devices commonly known as "closed urinary drainage units".

Closed urinary drainage units are well known medical devices, manufactured by several sources in the United States and elsewhere. A device of this type is, for example, manufactured by the Bard Corporation of Murry Hill, New Providence, N.J. A further such device is also manufactured by Intermed, Inc., of Sparta, N.J. The said drainage units are utilized in connection with medical patients who have undergone surgery, or other treatment, impairing normal urinary function. In these instances, the said closed drainage units are connected by suitable tubing and catheter means to the patient's urinary drainage ducts, and serve to accumulate urine which would otherwise be collected and discharged via the patient's bladder.

In general, these closed urinary drainage units comprise a flexible plastic container which may be openable at the bottom in order to enable drainage of the same, if desired, and which include an upwardly extending flexible filler tube, which projects from the top of the drainage unit. The said units, in addition, commonly employ one or more mounting means (e.g. hooks or so forth), which are arranged along the upper edge of the said unit. These means serve to mount the said units at any convenient surface. For example, if a patient utilizing a said unit is confined to a wheelchair or bed, the said unit may be attached to a convenience point on the environment, such as a bed railing, a portion of the wheelchair frame, or so forth.

In those instances (which are increasingly common, due to advances of medical technology and practice), wherein a patient normally utilizing this type of drainage unit is partially or fully ambulatory, a series impediment arises to the patient's continuing recovery and restoration of a healthy and normal state of mind. In particular, the said drainage units are both unsightly and embarrassing to the patient, especially under those circumstances where the patient desires to engage in otherwise normal activities and social intercourse. Under these conditions, the said units present a considerable and highly undesirable barrier to the patient's reentering the real world of commerce and personal relations.

Pursuant to the foregoing, it may be regarded as an object of the present invention to provide an enclosure or cover for receiving therein a bodily fluid drainage unit, which cover is effective in attractively concealing the said unit, thereby aiding and encouraging patient rehabilitation.

It is a further object of the invention to provide a cover as above, which while attractively concealing the fluid drainage unit at the same time assures continuing functioning of the unit without any impairment whatsoever of same.

It is a further object of the present invention, to provide an enclosure or cover of the aforementioned character, which includes additional fluid impervious features, thereby further safeguarding the possibility of spillage or leakage from the bodily drainage unit, even where a defect is present in same, or if a minor leakage should develop.

It is a still further object of the present invention, to provide a cover unit of the aforementiond character, which includes features acting to stabilize the flexible filler tube used with the said drainage units, so as to decrease the likelihood of any breakage or damage to same during use of the unit.

It is a still further object of the present invention, to provide an enclosure of the aforementioned type, which is adapted to readily receive and substantially completely enclose the said drainage unit to attractively conceal same; which is readily openable to remove the unit for service or otherwise; and which further, may include features enabling drainage of the contained unit without requiring complete removal of the drainage unit from the covering unit.

It is a yet additional object of the invention to provide a cover or enclosure of the aforementioned character, which while concealing a bodily fluid drainage unit therein in a manner rendering the total assembly attractive to the eye, does not impair in any way the use of the said drainage unit; which serves to facilitate the user's engagement in normal business and travel activities; and which further, permits the hanging feature otherwise associated with these drainage units to remain fully intact, to enable hanging of the totality including the drainage unit and the enclosure, on a convenient surface.

SUMMARY OF INVENTION

Now, in accordance with the present invention, the foregoing objects, and others as will become apparent in the course of the ensuing specification, are achieved in an enclosure which is utilized in combination with a conventional bodily fluid drainage unit. The said bodily fluid drainage unit is of the type which comprises a flexible plastic bag having an upwardly extending flexible filler tube for receiving bodily fluids from a patient. This bag is provided with at least one hanger means extending from the upper end of the bag for normally enabling attachment of the unit to a receiving surface associated with the patient's environment.

In accordance with the invention, the enclosure receives the drainage unit to attractively conceal same while simultaneously not impairing the functioning of the drainage unit.

The enclosure comprises a generally flattened flexible envelope openable along one end for receiving the drainage unit, the openable end being provided on its opposing facing edges with closure means, preferably in the form of continuous Velcro ® type strips, to enable closure of that end. The said strips in effecting the closure, simultaneously enable nesting of the upwardly extending flexible filler tube of the drainage unit, to prevent accidental dislodgement of same from the flexible bag or other damage to the filler tube or to the joint between the tube and the flexible bag.

The envelope is provided at one flattened surface of same, and adjacent to the openable end, with one or more buttonhole type openings which extend through the envelope into the interior of same. These openings are alignable with the hanger means of the drainage unit when the latter is placed within the envelope, whereby the hooks or other elements comprising or forming parts of the hanger means, may be received through the button type openings to enable the hanging function of these members.

The enclosure of the invention may be of substantially one piece construction, and in one embodiment is openable only at the mentioned one end of same, and is lined interiorly with a flexible plastic layer to prevent spillage or discharge of liquid from the interior of same.

The said envelope in a further embodiment, may include a second openable portion at the end of the envelope opposed to the first openable end. This enables discharge from the bottom of a drainage unit contained within the envelope. Alternatively, instead of a second fully openable portion opposed to the first openable end, a slot may be provided for drainage at the said opposed end.

The envelope itself may comprise a fabric, plastic or other material; and is preferably of an aesthetically attractive appealing design, and may be manufactured in a variety of colors, patterns, etc., to suit the dictates of the user.

BRIEF DESCRIPTION OF THE DRAWINGS

The invention is diagrammatically illustrated, by way of example, in the drawings appended hereto in which:

FIG. 9 is a perspective view similar to FIG. 1, showing use of the FIG. 1 device in association with a further type of drainage unit; and FIG. 10 is a fragmentary perspective view similar to FIG. 9, but showing the drainage unit partially removed in order to better illustrate certain of the latter's features.

DESCRIPTION OF PREFERRED EMBODIMENTS

Figure 1:
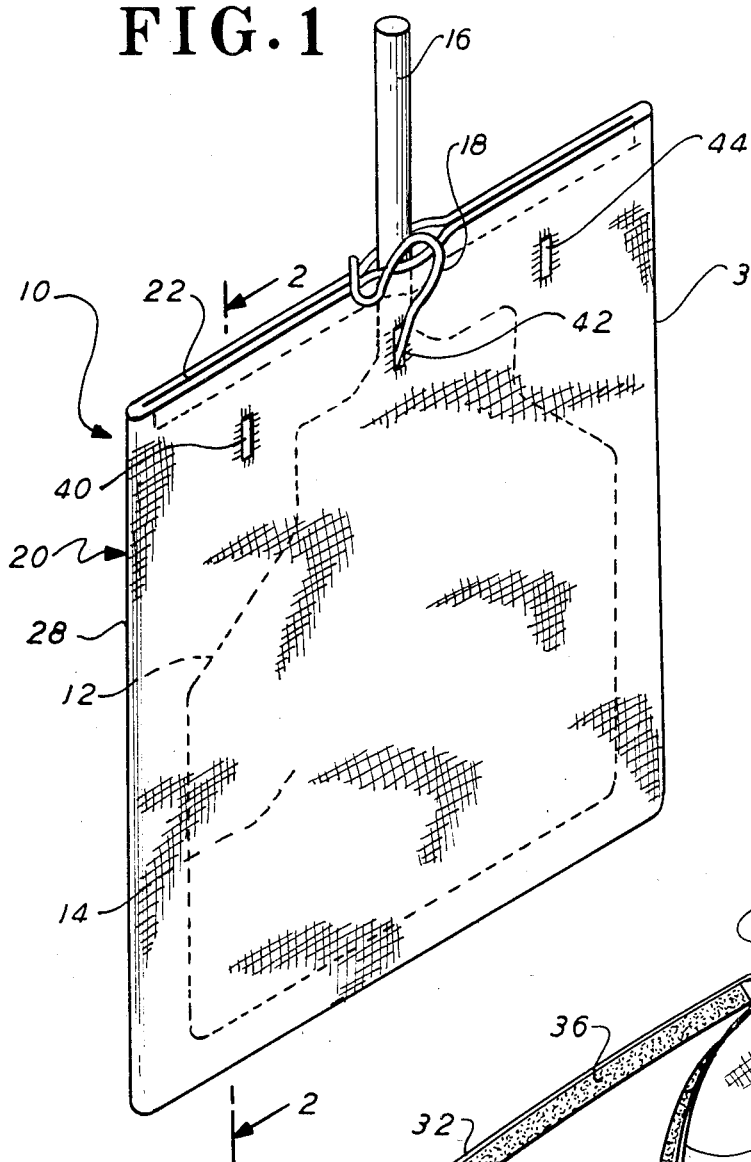
FIG. 1 is an external perspective view of an enclosure in accordance with the invention, in use with a bodily fluid drainage unit contained within the interior of the enclosure.

In FIG. 1 hereof, a perspective view appears of an enclosure 10 in accordance with the present invention, the said enclosure being utilized to house therein a bodily fluid drainage unit which is indicated in shadow at 12.

The drainage unit 12 is of the type previously described, which is conventional and produced by several manufacturers. The device 12 in the Figure is actually similar to the product produced by Intermed of Sparta, N.J., under catalog No. 620. The invention, however, is equally applicable to other such units, e.g. the types available from Bard Corporation of Murray Hill, New Providence, N.J. These units generally consist of a flexible plastic bag 14 of vinyl or other flexible material which is resistent to bodily fluids such as urine or so forth. The top of the bag 14 is connected to a flexible upwardly extending filler tube 16, which normally is connected via a suitable catheter to a patient to enable proper drainage. The said device, further, is conventionally (as shown) provided with a hanger means, which in the embodiment of FIG. 1 is in the form of a hook 18. In normal prior use of these flexible plastic drainage units, the said unit is hung from any convenient surface. For example, if the patient is confined to a wheelchair the said unit can be hung from an arm or other portion of the wheelchair frame; or if the patient is bedridden than the said unit may be attached to portions of the bed frame. Similarly, if the patient is rehabilitated, the unit can be hung from a normal chair, table frame, or the like. The normal gravitational drainage from the patient then fills the plastic bag, which normally, however, provides a rather unsightly and unaesthetically unappealing appearance. While this is not necessarily a problem where the patient is dangerously ill and confined to a hospital room or so forth, where the patient is ambulatory or receiving visitors, as is frequently the case thanks to modern technology, the said unattractive transparent plastic bag presents a serious psychological barrier to re-entry of the patient into normal life.

In accordance with the present invention, it is seen that the enclosure 10 is designed to completely contain in its interior the said drainage unit 12. The enclosure 10 is seen to comprise a generally flattened flexible envelope 20, the exterior of which can be formed of fabric or of plastic or the like, and which is preferably provided with any convenient and aesthetically appealing design. These designs can be floral, can include plain backgrounds against which animal figures or the like are present, or can comprise any other fanciful design which appeals or can appeal to the user.

In the embodiment of FIG. 1, the said envelope 20 is seen to be closed in its entirety along all sides except for the end 22. The said unit accordingly comprises opposed flat rectangular panels 24 and 26, which are joined at their lateral sides by foreshortened U-shaped sections 28 and 30, and is only openable at the upper end 22.

Figure 2:
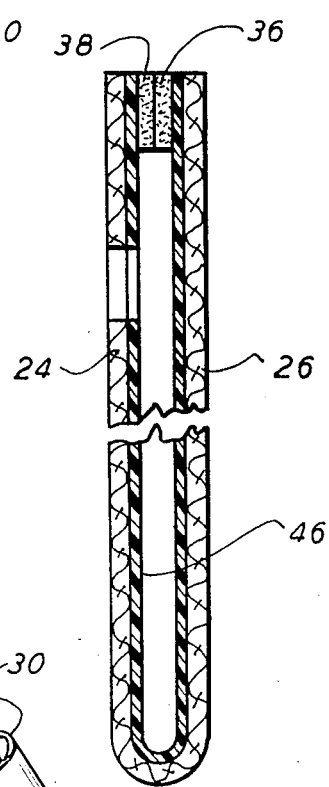
FIG. 2 is a longitudinal cross-sectional view of the device of FIG. 1, taken along the line 2—2 of FIG. 1.
Figure 3:
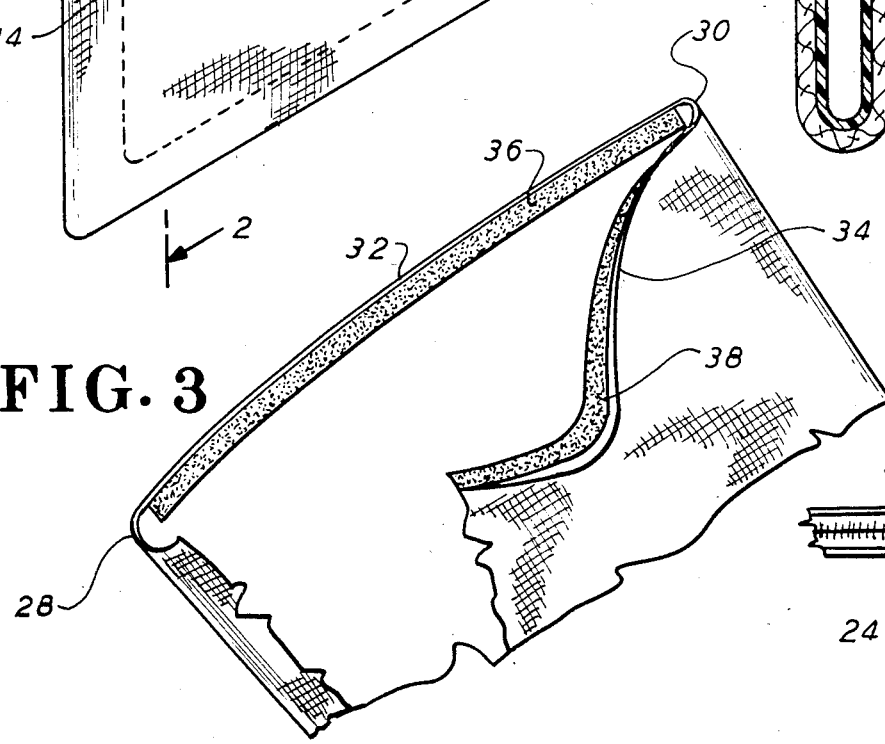
FIG. 3 is a partial perspective view of the top portion of the device of FIG. 1, with the openable end being shown in an open position to illustrate the Velcro ® fastening means provided along the opposed edges of the device.

As may be best seen from FIGS. 2 and 3, the mutually facing portions 32 and 34 of the panels 24 and 26 which adjoin the openable end, are respectively provided interiorly with continuous strips 36 and 38 of Velcro ® type fasteners, which extend continuously along the facing portions of the panels between the U-shaped sections 28 and 30. While generally not as effective, other closure means can also be used, such as mechanical mateable interfit strips of the ZIP-LOK ® type, etc.

It is further seen that at least one of the panels is provided with one or more button-type openings, as at 40, 42 and 44, beneath the respective Velcro ® strip. These openings serve to receive the hanging means, e.g. hook attachment means 18 of the drainage unit when same is received within enclosure 10, to thereby enable the enclosure including the drainage unit to be hung upon a receiving surface in the patient's environment.

Figure 4:
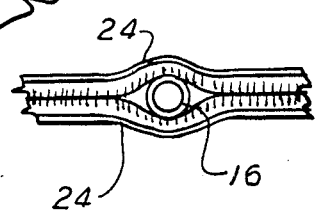
FIG. 4 is a partial top end view of the device of FIG. 1, showing the manner in which the flexible tube filler from the drainage unit is nested by the present device.

It will be noted from FIGS. 1 and 4 that the flexible filler tube 16 extends upwardly, and as a result of the opposed Velcro ® strips 36, 38, the said flexible tube is tightly nested by the said closure and Velcro ® strips. This serves an important function in stabilizing the said filler tube and preventing same from undue flexure, which can damage same, even in some instances causing a disruption of the connection between the tube and the flexible bag 14. It may be parenthetically noted that even the "possibility" of the tube disruption, as perceived by the patent, generates great anxiety for such patient—an anxiety much relieved by the stabilizing characterics of the present arrangement.

As best seen in FIG. 2 the embodiment of FIGS. 1 through 4 is provided substantially in the entire interior of same, with a flexible, liquid-impervious plastic lining 46, as for example a thin vinyl or other plastic envelope, which prevents spillage or discharge of liquid from the interior of the enclosure in the event any such liquid should leak, or in some manner be discharged from the drainage unit.

As may be seen from FIG. 1, there are actually three button-hole type openings 40, 42 and 44 provided. This is intended to enable the said enclosure to accommodate a variety of drainage units, since in some instances but a single hanger member is provided at the center of the drainage unit, whereas in other instances, a pair of such members—i.e. hooks may be provided. In the latter instance these can be passed through the openings 40 and 44.

Figure 5:
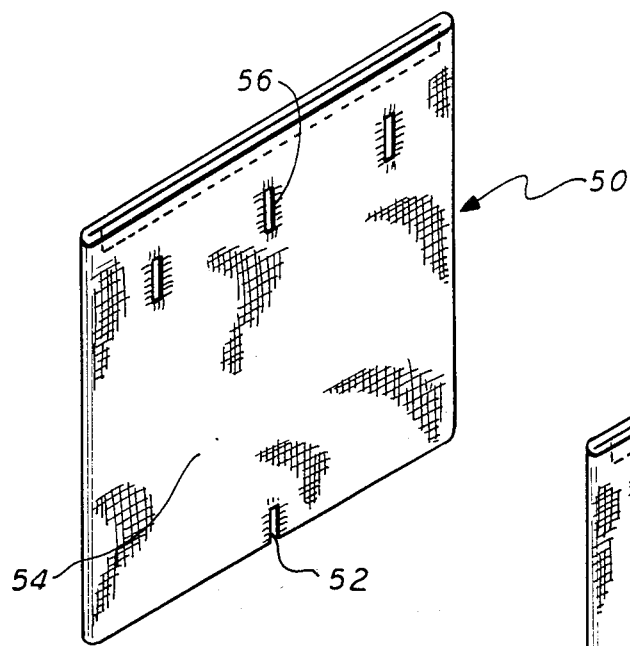
FIG. 5 is a perspective view of a second embodiment of the present invention.

In FIG. 5, a further embodiment of the present invention appears. The enclosure 50 is substantially identical externally to the device of FIG. 1, and can be formed of fabric as aforementioned. In this instance, however, it is seen that a slot 52 is provided at the bottom of the flexible envelope 54. This enables, if desired, a drainage port from the bottom of an interiorly contained fluid drainage unit. Since the device of FIG. 5 includes an opening at the bottom, there is no advantage in such arrangement to having the envelope lined interiorly with a plastic liner as is shown in the FIG. 1 device and FIG. 2. Also to be noted is that the embodiment of FIG. 5 includes but a single button-type opening which in this instance is centrally located at 5.

The device of FIG. 5 can also be formed of a flexible plastic, e.g., a vinyl or the like, which while not usually as attractive as a fabric, enables a very low cost, economical, and yet effective unit.

Figure 6:
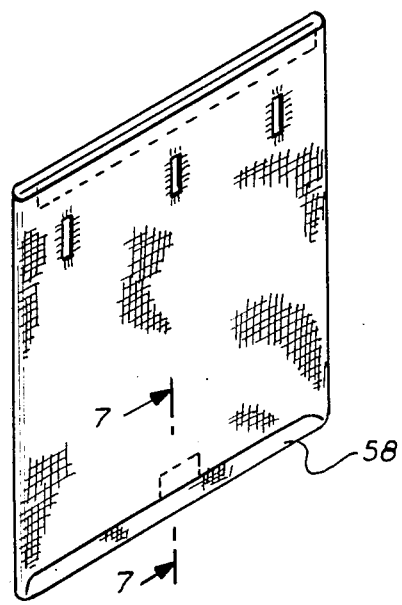
FIG. 6 is a perspective view of a third embodiment of the present invention, which includes an openable flap at the bottom of same.
Figure 7:
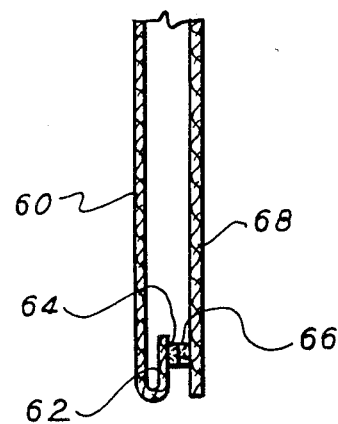
FIG. 7 is a partial longitudinal cross-sectional view, taken along the line 7—7 of FIG. 6.

A further embodiment of the invention appears in FIG. 6. In this instance, as may be seen from by simultaneous reference to FIG. 7, the embodiment is generally similar to FIG. 5, except instead of having a simple opening at the bottom of the device as in FIG. 5, an openable flap 58 is provided. This flap is formed by a portion 62 of panel 60 being turned upwardly as indicated in FIG. 7, and being provided at its upwardly extending portion with a piece 64 of Velcro ® fastener, which in turn engages a mating portion 66 of Velcro ® at the interior of panel 68. Again in the instance of the embodiments of FIGS. 6 and 7, since an opening is indeed provided for emptying the drainage unit at the bottom of the said device, there is no reason or advantage to an interior liquid impervious liner, and that type of liner is not used in this embodiment.

Figure 8:
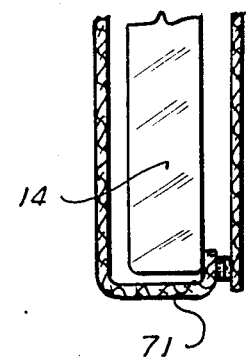
FIG. 8 is a view similar to FIG. 7, but showing the manner in which the structure of FIG. 7 may respond as the contained drainage unit fills.

In FIG. 8, a fragmentary view, similar to FIG. 7, appears. The said view, however, illustrating certain advantages associated with the embodiment of FIGS. 6 and 7.

In particular, it is seen that the said embodiment is susceptible to ready expansion at the bottom end thereof, so that when the flexible drainage unit including the flexible bag 14 is contained within the said embodiment, the opposed flat panels may readily expand when the bag 14 fills, as in FIG. 8. Indeed it is seen that the expansion of this embodiment of the cover produces a relatively flat bottom portion 72 as the expansion occurs.

In FIG. 9, a perspective view appears of the device 10 described in connection with FIGS. 1 through 4. In this instance, however, there is housed within the said device a somewhat different form of drainage unit than discussed in prior Figures. In particular, the unit 72 is a further type of conventional drainage unit, which is characterized, in this instance, as including a flexible plastic bag 74 (see FIG. 10 showing the bag 74 partially removed to accentuate certain features), which bag tapers somewhat toward its upper end, and which is seen to be provided with an extending flexible plastic strap 76. In this instance, the strap 76 serves a part of the hanging means for the unit when it is used conventially, i.e., not with the present invention. In that conventional use, the strap 76, which also serves in part to support the filler tube 78, is provided with a series of openings 80, 82, 84 and 86, which, when the strap is looped over, engages the button-like projection 88 at the bottom end of the strap. This provides a loop 90, which is secured about some convenient hanging point, or used as a hanger directly.

As seen in FIG. 9, the present invention is equally applicable to this type of drainage unit, since the button-like projection 88, forming part of the hanging means, may be received through the opening 56 of device 10, upon which the strap 76 as aforementioned, is brought about to form a loop and secured to the projection 88 which protrudes through opening 56.

Thus, as seen in FIGS. 9 and 10, in the instance of the drainage unit 72, the device 10 of the invention again serves to not only contain the drainage unit, attractively concealing same; but serves as well to nest and stabilize the filler tube 78, in conjunction with receiving the hanger means as in prior embodiments.

While the present invention has been particularly set forth in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

I claim:

1. In combination with a bodily fluid drainage unit of the type comprising a flexible plastic bag having an upwardly extending flexible filler tube connectible to a patient for receiving bodily fluids; and said bag being provided with at least one hanger means extending from the upper end of same for enabling attachment of said bag to a receiving surface associated with the patient's environment; an enclosure for receiving said drainage unit therein to attractively conceal same, while simultaneously not impairing the functioning of said unit; said enclosure comprising:

a generally flattened flexible envelope openable along one end thereof for receiving said drainage unit, said openable end being provided on the opposed facing edges with mateable closure means to enable closure of said end, and for enabling simultaneous nesting and stabilizing of the upwardly extending flexible filler tube of said drainage unit by said surrounding closure means; and said envelope being provided at one flattened surface thereof, and adjacent to the said openable end, with at least one button-hole type openings extending through said envelope into the interior of same, said openings being alignable with said hanger means of a said drainage unit emplaced within said envelope, to receive said hanger means through the openings, to enable the hanging functioning of same.

2. A device in accordance with claim 1, wherein said closure means comprise opposed continuous Velcro ® strips.

3. A device in accordance with claim 2, wherein the said enclosure is of substantially one piece construction; is openable only at said one end; and is lined interiorly with a flexible plastic layer to prevent spillage or discharge of liquid from the interior of same.

4. A device in accordance with claim 2, wherein said envelope includes a second openable portion at the end of said envelope opposed to said first openable end, for enabling discharge from the bottom of a said drainage unit contained within said envelope.

5. A device in accordance with claim 2, including a slot-like opening at the end opposed to said openable end, for enabling discharge from the bottom of a drainage unit contained within said envelope.

6. An enclosure for receiving therein a bodily fluid drainage unit, in order to attractively conceal same while assuring continuing functioning of said unit; said drainage unit being of the type comprising a flexible plastic bag having an upwardly extending flexible filler tube connectible to a patient for receiving bodily fluids, and at least one attachment means toward the upper end of said bag for hanging said drainage unit upon a receiving surface associated with the patient's environment; said enclosure comprising:

a substantially one-piece flexible envelope, having opposed flat rectangular panels joined at their lateral sides by foreshortened U-shaped sections, to thereby define a generally rectangular enclosure for said drainage unit, said envelope being openable at the upper end of same to receive the said drainage unit; the mutually facing portions of said panels adjoining said openable end being respectfully provided with continuous strips of Velcro ® type fasteners extending continuously along the facing portions of said panels between said U-shaped sections; and at least one of said panels being provided with at least one button-hole type opening beneath the said respective Velcro ® strip, for receiving therethrough the attachment means of said drainage unit when same is received within said enclosure, to thereby enable said enclosure including said drainage unit to be hung upon a receiving surface in the patient's environment;

said Velcro ® fasteners closing the said openable upper end of said flexible envelope, and acting to nest and stabilize the upwardly extending tube portion of said bodily fluid container as same extends from said openable end of said envelope.

7. A device in accordance with claim 6 wherein substantially the entire interior of said flexible envelope is lined with a flexible, liquid-impervious plastic, to prevent spillage or discharge of liquids from the interior of said enclosure.

8. A device in accordance with claim 6, wherein three of said button-hole type openings are provided along the said panel, one being central and the others toward the alternate lateral sides of said panel, to enable receipt therethrough of either a pair of said attachment means through the said openings at the alternate sides of said enclosure, or a single said attachment means through the central of such openings.

9. A device in accordance with claim 6, including an opening at the bottom of said envelope, for enabling emptying of a drainage unit therein by a discharge means provided at the bottom of said drainage unit.

10. A device in accordance with claim 9, wherein said bottom opening includes an openable flap which is normally closed by a Velcro ® type fastener.

* * * * *